US005750405A

United States Patent [19]
Albarella et al.

[11] Patent Number: 5,750,405
[45] Date of Patent: May 12, 1998

[54] METHOD FOR THE DETECTION FOR PROTEIN

[75] Inventors: James P. Albarella, Granger, Ind.; Sally E. Cahill, Union, Mich.; Gary M. Johnson, Elkhart; Michael J. Pugia, Granger, both of Ind.

[73] Assignee: Bayer Corporation, Pittsburgh, Pa.

[21] Appl. No.: 609,674

[22] Filed: Mar. 1, 1996

[51] Int. Cl.$^6$ .................................................. G01N 33/96
[52] U.S. Cl. ............................ 436/88; 436/169; 422/56
[58] Field of Search ............................ 436/86, 88, 169; 422/56–58

[56] References Cited

U.S. PATENT DOCUMENTS

| | | | |
|---|---|---|---|
| 5,124,266 | 6/1992 | Coryn et al. | 436/86 |
| 5,187,104 | 2/1993 | Corey et al. | 436/86 |
| 5,424,215 | 6/1995 | Albarella et al. | 436/86 |

OTHER PUBLICATIONS

Y. Fujita, Bunseki Kagaku (32) 379–386 (1983) "Color Reaction Between Pyrogallol Red–Molybdenum(VI) Complex and Protein".

Kragh–Hansen, Biophysics Acta, (365), 360–371 (1974) "Protein Binding of Small Molecules".

Macart et al, Clinica Chimica Acta (141), 77–84 (1984) "Evaluation of an Improved Coomassie Dye Binding Method for Urinary Protein Assay".

Primary Examiner—Lyle A. Alexander
Attorney, Agent, or Firm—Jerome L. Jeffers

[57] ABSTRACT

The determination of human serum albumin (HSA) in urine is carried out by contacting the urine with a reagent system containing a buffer and a protein error indicator. Other proteins normally found in urine can compete with the HSA for interaction with the protein error indicator thereby affecting the sensitivity of the test for HSA. The present invention involves the addition of certain polymeric competitive inhibitors to the reagent system which inhibit the interaction of the urinary proteins other than HSA with the protein error indicator to a greater extent than the interaction with HSA is inhibited thereby increasing the reagent's sensitivity for HSA. Suitable polymeric inhibitors include poly(vinyl alkyl esters), poly(alkyl acrylates), poly(vinyl alkyl carbonates) and poly(vinyl alkyl ketones).

18 Claims, No Drawings

METHOD FOR THE DETECTION FOR PROTEIN

BACKGROUND OF THE INVENTION

The present invention relates to the detection of protein in aqueous fluids, e.g. urine, by the use of a test system containing a protein error indicator and a buffer. The determination of the presence of protein in a urine sample is important in the diagnosis of several pathological conditions affecting the kidney, circulatory and central nervous systems. It is often necessary to qualitatively and quantitatively measure protein in urine, especially in connection with the diagnosis of diabetes and kidney disease. The predominant urine protein associated with diabetes is albumin which is the protein most commonly sought out in analysis.

Various methods for determining the presence of protein in urine are known, the most convenient of which involves wetting an absorbant strip impregnated with a protein error indicator and buffer with a small quantity of urine. Protein error indicators are pH indicators which contain an ionizable group which is displaced in the presence of protein to provide a detectable color change. This is the same color change that the indicator would undergo under the influence of a pH change, so it is important to include a buffer in the test system to thereby avoid a pH increase since such an increase could cause the color change in the indicator in the absence of protein thereby resulting in a false positive result.

Protein detection methods based on the binding of protein error indicators such as phenolsulfonephthalein dyes are relatively nonspecific means of protein determination. The present invention involves the use of certain competitive inhibitors to increase the specificity of methods based on the binding of protein error indicators.

U.S. Pat. No. 5,187,104 discusses the use of DIDNT dye in a protein detection method and mentions the use of color enhancing polymers in combination with the reagents. Specific polymers mentioned are polypropylene glycols, poly (propylene ether carbonate), and polyvinylethers. Also mentioned is the polyether carbonate designated as KOK 10,002 from Bayer AG, a propylene oxide and ethylene oxide adduct of 1,6-dimethyl-4-nonylphenol available from Bayer AG under the tradename Fenoil D4030 and a polyvinyl ether available under the designation Lutonal ISO from BASF.

In U.S. Pat. No. 5,124,266 there is described the use of a test strip for protein in urine in which a bibulous carrier matrix containing a protein error indicator and a buffer is treated with a polymerized urethane based compound to resist the formation of background color to thereby improve the sensitivity of the test strip.

The use of polyvinyl alcohol and poly(vinyl carboxylic acid) has been described as a binder to prevent buffer from running off the reagent pad in U.S. Pat. No. 5,424,4215 to Albarella et al. However, there is no discussion of these polymers' ability to increase or alter the specificity of the method for one protein over another.

The use of polyvinyl alcohol has been described in conjunction with protein tests based on metal chelating dyes by Y. Fujiti in Bunseki (32) 379–386 (1983). This reference describes polyvinyl alcohol and polyvinyl pyrrolidone as suitable nonionic surfactants for unicell formation but does not mention any increase in the specificity for albumin.

Several studies have been carried out on the effects of long chain alkyl groups on the binding of protein error indicators to proteins. The effects of long chain alkyl carboxylic acids, such as palmitic acid, on the binding of protein error indicators has been described by Kragh-Hansen in Biophysics Acta, (365), 360–371 (1974). Palmitate was shown to have modest inhibitory effects on the binding of phenol red to albumin; other proteins were not studied. Based on this, one would not expect long chain alkyl groups to alter specificity.

Other studies have shown that long chain alkyl sulfonic acids, such as sodium dodecyl sulphate, affect the binding of protein error indicators. Work described by Macart et al in Clinica Chimica Acta (141), 77–84, (1984), Perini et al in Clinica Chimica Acta (143), 321–328, (1984) showed that sodium dodecyl sulfate equalized the differences in the sensitivity of Coomassie Brilliant Blue (CBB) to various proteins and decreased the specificity of the test for albumin. Based on this result, one would expect long chain alkyl groups to decrease the system's specificity for albumin.

SUMMARY OF THE INVENTION

The present invention involves the semi-quantitative analysis of human serum albumin in an aqueous test sample which is carried out by contacting the fluid suspected of containing this protein with a test reagent comprising a protein error indicator dye which undergoes a detectable color change when contacted with protein. There is presently disclosed an improvement which comprises adding to the test reagent a competitive inhibitor characterized by formula A:

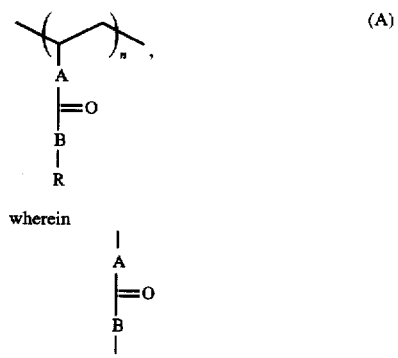

a linking group in which A and B can be a single bond or oxygen so that when A is oxygen and B is a bond the polymer is a poly(vinyl alkyl ester), when A is a bond and B is oxygen, the polymer is a poly(alkyl acrylate), when A is oxygen and B is oxygen, the polymer is a carbonate and when A is a bond and B is a bond the polymer is a poly(vinyl alkyl ketone). The R substituent is a straight, branched or cyclic alkyl group of 1 to 20 carbon atoms in which 0 to 10 hydrogens can be replaced by hydroxyl groups, the polymer backbone comprises repeating alkyl or carbonate, e.g. cellulose or glucoamine, subunits which can be co-polymerized with unreactive blocking units and the number of alkyl groups attached to repeating polymer subunits through the linking groups ranges from 10% to 90% of the theoretical maximum.

DESCRIPTION OF THE INVENTION

In accordance with the present invention, it has been discovered that certain polymeric inhibitors reduce the response of a protein error indicator to proteins in the protein error indicator test under consideration. Those particular polymers that inhibit the protein error indicator response to human serum albumin (HSA) to a lesser degree than the response to other proteins normally found in urine are desirable additives to a reagent for determining the concentration of HSA, because of the resulting increase in specificity for HSA which such a system provides. Those polymeric inhibitors which are useful in the present invention are represented by formula A. The polymers represented by this formula can be poly(vinyl alkyl esters), poly(alkyl acrylates), poly(vinyl alkyl carbonates) or poly(vinyl alkyl ketones). Various polymers that have been found to be useful in the present invention are set out in Table 5. In the case of poly(vinyl alkyl esters), i.e. polymers in which A is oxygen and B is a bond in the foregoing formula, specific polymers in addition to those set out in Table 5 include, but are not limited to cases where the alkyl groups are, cyclohexanoate, trans-5-decanoate, 10-hydroxydecanoate and 5-hydroxydecanoate. When a poly(alkyl acrylate) is used, i.e. A is a bond and B is oxygen, suitable polymers in addition to those listed in Table 5 include those in which the alkyl groups are octyl, cyclohexyl, dicyclohexyl and 5-methylhexyl. Particular poly(vinyl alkyl carbonates), i.e. polymers according to the foregoing formula in which both A and B are oxygen, in addition to those set out in Table 5 include those in which the alkyl groups are nonadecyl, decyl, 4-hydroxyheptyl and cyclopentyl, whereas poly(vinyl ketones) which are represented when both A and B are bonds include alkyl groups such as butyl, decyl, neodecyl and octadecyl as well as those in Table 5. The molecular weights of these polymers are not critical to their usefulness in the present invention although those in which the degree of polymerization (n) ranges from about 20 to 40,000 are preferred due to their ability to adhere to the surface of the HSA molecule.

One aspect of the present invention is directed to an analytical test strip for the detection of HSA in urine which strip comprises an absorbant carrier impregnated with a suitable protein error indicator, a suitable buffer and the polymeric inhibitor. Suitable protein error indicators include Tetrabromophenol Blue (TBPB), 5',5"-Dinitro-3'3"-Diiodo-3,4,5,6-Tetrabromophenolsulphonephthalein (DIDNTB), Coomasie Brilliant Blue, Fast Green FCF, Light Green SF, pyrogallol red and pyrocatechol violet. In addition the merocyanine and nitro or nitroso substituted polyhalogenated phenolsulfonephthaleins disclosed in U.S. Pat. No. 5,279,790 may be used.

The absorbant carrier of the test strip is preferably filter paper, other materials useful as the absorbant carrier include felt, porous ceramic strips and woven or matted glass fibers such as those described in U.S. Pat. No. 3,846,247. Also suitable are wood, cloth, sponge material and argillaceous substances such as those described in U.S. Pat. No. 3,552,928. Alternatively, the absorbant carrier can be of a nonporous material such as a polymeric film or glass.

In preparation of the strip, the absorbant carrier is impregnated with a solution of the protein error indicator, buffer and the polymeric inhibitor. This impregnation is normally carried out by a two dip procedure in which the first dip comprises water or a water/polar organic solvent mixture in which there is dissolved a buffer. After drying, the strip is dipped into a second solution of an organic solvent in which is dissolved the protein error indicator which is typically present at a concentration of from about 0.2 to 5.0 mM and the polymeric inhibitor.

After dipping and drying, the strips are ready for use which normally involves dipping them into a urine sample and reading the response resulting from the color change in the indicator which reading is conducted either manually or by use of a reflectance spectrometer for better quantitation.

The pH at which the assay is conducted will depend on the particular dye which is used in the reagent formulation. The buffers which are most compatible with a particular dye are known or can be readily determined through routine experimentation.

The method of practicing the present invention is further illustrated by the following examples. These examples and the data contained therein demonstrate the desiratbility of using polymers, as described by the foregoing general structure, to increase the specificity of the dye binding method for human serum albumin (HSA). This method enhances the diagnostic value of urinary HSA determinations and allows more accurate assessments of kidney health.

EXAMPLE I

The HSA specificity of a phenolsulfonephthalein dye [5',5"-dinitro-3',3"-diiodo-3,4,5,6-tetrabromophenolsulfonephthalein (DIDNTB)] was measured in the presence of increasing concentrations of several types of polymeric and non-polymeric additives. Also tested were certain long chain substituted alkanes. The general structure of the additives tested is set out in the following Scheme I.

| Scheme I |  |
|---|---|
| 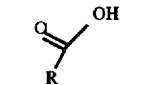 | |
| R | Name |
| $C_9H_{19}$ | Decanoic acid |
| $C_{15}H_{31}$ | Hexadecanoic acid |
| 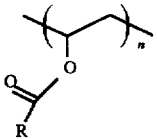 | |
| R | Name |
| $C_{17}H_{35}$ | Poly(vinyl stearate) |
| 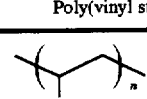 | |
| R' | Name |
| H | Poly(vinyl alcohol) |
| 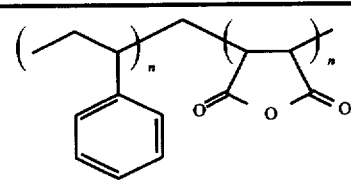 | |
| R | Name |
| $CO_2H$ | Poly(acrylic acid) |
| $SO_3H$ | Poly(vinylsulfonic acid) |
| $CONC(CH_3)_2CH_2SO_3H$ | Poly(2-acrylamido-2-methyl-1-propanesulfonic acid) |
| $C_6H_4SO_3Na$ | Poly(sodium-4-styrene sulfonate) |
| | Name |
| | Poly(styrene maleic acid co-polymer) |

These measurements were carried out as follows:

The DIDNTB protein reagent was made from two saturations of Alhstrom 204 filter paper in which the first saturation was made with an aqueous ethanol mix containing tartaric acid as buffer and methyl red as background dye. The pH was adjusted to 2.1. The second saturation was with a toluene/tetrahydrofuran mix containing the DIDNTB indicator dye and Lutanol M40 (a polyvinylmethylether) as a color enhancer polymer.

Water soluble additives such as poly vinyl alcohol), poly(vinylsulfonic acid) and poly(2-acrylamido-2-methyl-1-propanesulfonic acid) were added to the first mix while water insoluble additives such as decanol, decanoic acid, hexadecanoic acid, poly vinyl stearate), poly styrene/maleic anhydride) and poly(sodium-4-styrene sulfonate) were added to the second mix.

The mix solutions were used to saturate the filter paper and the paper was dried at 105° C. for 7 minutes after each saturation. The resultant dry reagents were processed into reagent strips which were tested on a Clinitek-200+ reflectance spectrophotometer from Bayer Diagnostics after dipping into urine containing 0 or 30 mg/dL human serum albumin or 40 mg/dL of another urinary protein. The particulars of each dip solution are set out in Table 3.

Prior to the addition of HSA, the urine sample was filtered through an ultrafiltration membrane having a 10 KDa (kilodalton) molecular weight cut-off to remove naturally occurring proteins. The total protein in the urine sample was determined using an immunological HSA assay and the Coomassie Brilliant Blue (CBB) method described by Perini et al as cited above to screen over 175 clinical samples to provide specimens lacking albumin but containing other urine protein. Four specimens out of 175 were identified with a total protein/HSA ratio of greater than 10; one sample had a ratio of 242. These urines were pooled and diluted with negative urine to 40 mg/dL by the CBB method and less than 1.2 mg/dL by immunological HSA assay. The reagent response was measured on the CLINITEK-200+ instrument as the result of 1000×% Reflectance @ 610 nm/% reflectance @ 690 nm. The difference between negative and protein containing urines was taken as the protein response. The data generated by this experiment are set out in Table 1 in which the protein response of control formula lacking polymer or substituted alkane additive is compared to the formulas containing polymer or alkane to determine the % change in response. Negative numbers indicate greater loss of protein response.

The HSA response in the presence of these additives was compared to the response for other urinary proteins such as Tamm Horsefall glycoprotein, Bence-Jones protein, α-1-microglobin, hemoglobin and various low molecular weight protein fragments. The additives were used at a 0.1% (w/w) concentration to allow a measurable HSA response in all cases. The data generated are set out in Table 2. The 0.1% concentration amounts to 10 to 20 µM concentration of additive and is in excess of the 4.4 µM concentration of the proteins tested. Only poly vinyl stearate) inhibited other urinary protein more than it inhibited HSA indicating that this polymer increases the specificity of the phenolsulfonephthalein method for albumin. Consequently poly vinyl stearate) increases the specificity of the phenolsulfonephthalein method for determining HSA in urine. Other additives either had no effect, being within 10% of control, or inhibited HSA and other urinary proteins equally as can be determined from Table 1. Since the presence of 6 mM of substituted alkanes such as decanol, decanoic acid and hexadecanoic acid did not affect the protein response, it can be determined that the effect of poly vinyl stearate) cannot be attributed to the alkyl group of the polymer alone.

TABLE 1

| | | % change in response | |
|---|---|---|---|
| | | Urinary proteins 40 mg/dL | HSA 30 mg/dL |
| No additive | | 0% | 0% |
| Decanol | 6 mM | 8% | 3% |
| Decanoic acid | 6 mM | 2% | 7% |
| Hexadecanoic acid | 6 mM | 1% | −2% |
| Poly(vinyl alcohol) | 0.10% | −4% | −7% |
| Poly(vinyl acrylic acid) | 0.10% | −5% | −6% |
| Poly(vinyl stearate) | 0.10% | −42% | −15% |
| Poly(vinylsulfonic acid) | 0.10% | −51% | −51% |
| Poly(2-acrylamido-2-methyl-1-propanesulfonic acid) | 0.10% | −38% | −39% |
| Poly(styrene/maleic anhydride) | 0.10% | −12% | −13% |
| Poly(sodium-4-styrene sulfonate) | 0.10% | −38% | −40% |

Only poly (vinyl stearate) decreased the sensitivity of the protein error indicator towards urinary proteins other than HSA more than it decreased the sensitivity for HSA and was selected as a successful inhibitor. Polymers containing sulfonic acids, alkyl or aromatic groups caused an equal loss of sensitivity for both HSA and other urinary proteins as indicated by Table 1. Poly(vinylsulfonic acid) and poly (sodium-4-styrene sulfonate) caused the greatest loss of sensitivity for HSA and other urinary proteins. The loss of sensitivity increased with increasing polymer concentration. On the other hand, polymers containing hydroxyl or carboxylic acid groups did not cause a loss of sensitivity for either HSA or other urinary protein even at high concentrations as shown in Table 2. These results indicate that several polymers can reduce the protein response of a protein indicator. However, in order for a polymer to be effective in improving specificity, the HSA response should be affected to a lesser extent than is the response for other types of proteins.

TABLE 2

The Effect of Polymer Concentration on HSA Sensitivity

| | % Inhibition of 30 mg/DL HSA | | | | | | | | |
|---|---|---|---|---|---|---|---|---|---|
| Concentration | 2.00% | 1.00% | 0.75% | 0.50% | 0.40% | 0.25% | 0.20% | 0.10% | 0.05% |
| Poly(2-acrylamido-2-methyl-1-propanesulfonic acid) | | 62% | 61% | | 61% | | 44% | 37% | 19% |
| Poly(sodium-4-styrene sulfonate) | | | | 92% | | | 69% | 42% | 18% |
| Poly(vinylsulfonic acid) | | | 71% | | 71% | | | 55% | 44% |
| Poly(vinyl alcohol) | 10% | −3% | | | | 3% | | | |
| Poly(vinyl acid) | 3% | | | | −4% | | −6% | | |

TABLE 2-continued

The Effect of Polymer Concentration on HSA Sensitivity

| | % Inhibition of 30 mg/DL HSA | | | | | | | | |
|---|---|---|---|---|---|---|---|---|---|
| Concentration | 2.00% | 1.00% | 0.75% | 0.50% | 0.40% | 0.25% | 0.20% | 0.10% | 0.05% |
| Poly(vinyl stearate) | 36% | | | | 26% | | 20% | 15% | |
| Poly(styrene/maleic anhydride) | 54% | 36% | | 24% | | 11% | | | |

TABLE 3

DIDNTB Protein Reagent Composition.

| Ingredient | Function | Conc. used | Allowable Range |
|---|---|---|---|
| 1st application | | | |
| Water | Solvent | 1000 mL | — |
| Methyl red | Background dye | 9.5 mg | 0–10 mg |
| Ethanol | Solvent | 100 g | 0–40 g % |
| Tartaric acid | Buffer | 64 g (280 mM) | 50–750 mM |
| Water soluble additive | | See Table 1 | 0.01 to 4 g % |
| pH | — | 2.1 | 1.5–3.5 |
| 2nd application | | | |
| Toluene | Solvent | 95 mL | — |
| THF | Solvent | 5 mL | 0–50 mL |
| DIDNTB | Indicator | 65.7 mg (0.6 mM) | 0.2–5.0 mM |
| Lutonal M40 | Polymer enhancer | 0.143 g % | 0–1.0 g % |
| Water insoluble additive | | See Table 1 | 0.01 to 4 g % |

EXAMPLE II

The specificity of DIDNTB dye was measured in the presence and absence of a series of alkyl polymers as set out in Scheme II.

Scheme II
Alkyl Polymers of Example 2.

| R | Name |
|---|---|
| CH$_3$ | Poly(vinyl acetate) |
| C$_2$H$_5$ | Poly(vinyl propionate) |
| C$_3$H$_7$ | Poly(vinyl butyrate) |
| (CH$_2$)$_5$CH(CH$_3$)$_2$ | Poly(vinyl neodecanoate) |
| C$_5$H$_{11}$ | Poly(vinyl hexanoate) |
| C$_9$H$_{17}$ | Poly(vinyl decanoate) |
| C$_{11}$H$_{23}$ | Poly(vinyl laurate) |
| C$_{17}$H$_{35}$ | Poly(vinyl stearate) |

| R | Name |
|---|---|
| H | Poly(vinyl alcohol) |
| CH$_3$ | Poly(vinyl methyl ether) (LUTANOL M-40) |
| C$_2$H$_5$ | Poly(vinyl ethyl ether) |
| CH$_2$CH(CH$_3$)$_2$ | Poly(vinyl isobutyl ether) |

| R | Name |
|---|---|
| COCH$_3$ | Poly(methyl vinyl ketone) |

| R | Name |
|---|---|
| C$_4$H$_9$ | Poly(butyl acrylate) |
| C$_4$H$_8$OH | Poly(4-hydroxybutyl acrylate) |
| C$_6$H$_{13}$ | Poly(hexyl acrylate) |
| C$_{10}$H$_{21}$ | Poly(decyl acrylate) |
| C$_{12}$H$_{25}$ | Poly(lauryl acrylate) |
| C$_{18}$H$_{37}$ | Poly(octadecyl acrylate) |

| R | Name |
|---|---|
| CH$_2$CH(CH$_3$)$_2$ | Poly(vinyl i-butylcarbonate) |

In order to relate this example to common practice, the specificity of DIDNTB dye was assessed with other polymers typically used in protein reagents. These polymers were Lutanol M40 (described in U.S. Pat. No. 5,424,215) KOK 10071 polymer (described in U.S. Pat. No. 5,424,215) and poly(vinyl alcohol). These polymers did not increase the specificity of DIDNTB dye for albumin. The KOK 10071 and Lutanol M40 polymers increased the sensitivity of the test for all proteins whereas PVA had no significant effect. This was expected based on the teachings of U.S. Pat. Nos. 5,187,104 and 5,424,125. The data generated in comparing these polymers are set out in Table 4.

TABLE 4

Comparison of Typical Polymers.

| | | Δ % R at 610 nm for | | | | |
|---|---|---|---|---|---|---|
| Formula containing | Concn. | 0–8 mg/dL HSA | 0–20 mg/dL Hb | 0–20 mg/dL TRANS | 0–300 mg/dL LYS | μg/pad Uptake |
| No palymer | 0.000% | 12.8 | 8.6 | 7.0 | 11.2 | 17.2 |
| Poly(propylene ether carbonate)(KOK10071) | 0.250% | 21.6 | 28.4 | 23.4 | 30.4 | 15.8 |
| Poly(vinyl alcohol) {PVA} | 0.250% | 10.8 | 7.1 | 5.4 | 7.6 | 16.8 |
| Poly(vinyl methyl ether) {Lutanol M40} | 0.100% | 22.1 | 28.6 | 23.1 | 26.2 | 15.8 |
| control {LUTANOL & KOK10071 & PVA} | as above | 20.0 | 33.4 | 24.2 | 16.2 | 15.3 |

Four groups of alkyl polymers with ether, ester, acrylate and carbonate linking groups were compared by addition to a control formula which contained the typically used polymers. The albumin (HSA), hemoglobin (Hb), transferrin (TRANS) and lysozyme (LYS) sensitivities of these formulas are compared in Table 5. Increased HSA specificity was indicated by a decreased sensitivity towards either hemoglobin, transferrin or lysozyme (i.e. 0%) with less of a decrease in sensitivity towards HSA (i.e. ≧100% being ideal).

TABLE 5

Comparison of Alkyl Polymers of Example 2.

| | | | % Response Relative to | | | | |
|---|---|---|---|---|---|---|---|
| Control Formula containing | Concn. | Id | 8 mg/dL HSA | 20 mg/dL Hb | 20 mg/dL TRANS | 300 mg/dL LYS | μg/pad Uptake |
| ETHER GROUP | | | | | | | |
| Poly(vinyl ethyl ether) | 0.025% | 6a | 92% | 88% | 85% | 91% | 12.3% |
| | 0.100% | 6b | 70% | 80% | 75% | | 8.8% |
| Poly(vinyl isobutyl ether) | 0.025% | 7a | 75% | 80% | 50% | 76% | 5.0% |
| | 0.100% | 7b | 32% | 28% | 10% | | 5.4% |
| ESTER GROUP | | | | | | | |
| Poly(vinyl acetate) | 0.025% | 8a | 98% | 99% | 84% | 42% | 12.1% |
| | 0.100% | 8b | 120% | 98% | 92% | | 13.0% |
| Poly(vinyl propionate) | 0.025% | 9a | 98% | 99% | 109% | 46% | 12.5% |
| | 0.100% | 9b | 41% | 53% | 33% | | 9.3% |
| Poly(vinyl butyrate) | 0.025% | 10a | 149% | 108% | 68% | 60% | 9.6% |
| | 0.100% | 10b | 22% | 20% | 6% | | 7.0% |
| Poly(vinyl hexanoate) | 0.025% | 11a | 128% | 50% | 10% | 23% | 8.1% |
| | 0.100% | 11b | 111% | 19% | 14% | | 5.1% |
| Poly(vinyl neodecanoate) | 0.025% | 12a | 58% | 61% | 16% | −12% | 8.3% |
| | 0.100% | 12b | 31% | 54% | 26% | | 8.9% |
| Poly(vinyl decanoate) | 0.025% | 25a | 45% | 15% | 15% | −4% | 11.2% |
| | 0.100% | 25b | 25% | 22% | 22% | | 7.4% |
| Poly(vinyl laureate) | 0.025% | 13a | 92% | 76% | 55% | 17% | 12.6% |
| | 0.100% | 13b | 0% | 8% | 16% | | 11.1% |
| Poly(vinyl stearate) | 0.025% | 14a | 111% | 102% | 94% | 43% | 13.6% |
| | 0.100% | 14b | 104% | 94% | 99% | | 12.9% |

TABLE 5-continued

Comparison of Alkyl Polymers of Example 2.

| Control Formula containing | Concn. | Id | % Response Relative to | | | | μg/pad Uptake |
|---|---|---|---|---|---|---|---|
| | | | 8 mg/dL HSA | 20 mg/dL Hb | 20 mg/dL TRANS | 300 mg/dL LYS | |
| KETONE GROUP | | | | | | | |
| Poly(methyl vinyl ketone) | 0.025% | 15a | 92% | 91% | 95% | 27% | 9.3% |
| | 0.100% | 15b | 110% | 96% | 101% | | 7.1% |
| ACRYLATE GROUP | | | | | | | |
| Poly(butyl acrylate) | 0.025% | 18a | 92% | 59% | 82% | 23% | 12.5% |
| | 0.100% | 18b | 64% | 46% | 12% | | 12.1% |
| Poly(4-hydroxybutyl acrylate) | 0.025% | 19a | 125% | 107% | 101% | 68% | 7.9% |
| | 0.100% | 19b | 77% | 99% | 93% | | 4.8% |
| Poly(hexyl acrylate) | 0.025% | 20a | 78% | 74% | 96% | 30% | 5.7% |
| | 0.100% | 20b | 43% | 39% | 38% | | 5.6% |
| Poly(decyl acrylate) | 0.025% | 21a | 56% | 50% | 65% | 1% | 9.1% |
| | 0.100% | 21b | 25% | 42% | 32% | | 6.9% |
| Poly(lauryl acrylate) | 0.025% | 22a | 113% | 94% | 100% | 27% | 10.9% |
| | 0.100% | 22b | 63% | 78% | 65% | | 9.9% |
| Poly(octadecyl acrylate) | 0.025% | 23a | 92% | 88% | 91% | 47% | 7.0% |
| | 0.100% | 23b | 91% | 77% | 71% | | 5.4% |
| CARBONATE GROUP | | | | | | | |
| Poly(vinyl i-butylcarbonate) | 0.025% | 24a | 29% | −9% | −9% | 9% | 8.3% |
| | 0.100% | 24b | 6% | 0% | −9% | | 7.2% |
| ESTER GROUP ON CARBOHYDRATE POLYMER | | | | | | | |
| Cellulose Butyrate | 0.105% | 25a | 88% | 82% | 78% | 43% | 8.7% |
| Cellulose Propionate | 0.105% | 26b | 83% | 79% | 73% | 39% | 9.3% |

From Table 5 it can be determined that ethers did not affect the specificity of the dye. Esters, acrylates, ketones and carbonates all improved specificity as shown by a decreased lysozyme sensitivity with either a constant or less reduced HSA sensitivity. The best specificity is observed with hexanoate, neodecanoate, decyl and decanoate alkyl groups. Polymers with these groups also reduced the hemoglobin and transferrin sensitivity. Branched and hydroxyl containing alkyl groups and a carbohydrate polymer backbone with an ester alkyl group were also effective.

The responses indicated in Table 5 are relative to the control formula lacking any alkyl polymer, and due to the variations in the determination results, only effects greater than 10% are considered significant. All formulations contained Lutanol, KOK and PVA in the concentrations mentioned in Table 4.

The experimental procedure for Example II involved two saturations from filter paper as in the previous example. The first saturation was with an aqueous ethanol mix containing a citric acid buffer and PVA as a binding polymer and the mix pH was adjusted to 2.1. The second saturation was a toluene mix containing a protein indicator dye (DIDNTB) and enhancer polymers (Lutanol M40 and KOK 10071). The mix solutions were used to saturate filter paper whereupon the paper was dried at 105° C. for 7 minutes after each saturation. The function, preferred concentration and allowable range of ingredients in the reagent formulation are set out in Table 6.

TABLE 6

| Ingredient | Function | Conc. used | Allowable Range |
|---|---|---|---|
| 1st application | | | |
| Water | Solvent | 1000 mL | — |
| Ethanol | Solvent | 100 g | 0–40 g % |
| PVA polymer | Binder | 0.25 g % | 0–5 g % |
| Sodium citrate | Buffer | 41.7 g | 50–750 mM |
| Citric acid | Buffer | 45.1 g | 50–750 mM |
| pH | — | 2.1 | 1.5–3.5 |
| 2nd application | | | |
| Toluene | Solvent | 95 mL | — |
| THF | Solvent | 5 mL | 0–50 mL |
| DIDNTB | Indicator | 0.329 g (3 mM) | 0.2–5.0 mM |
| Lutonal M40 | Polymer enhancer | 0.100 g % | 0–1.0 g % |
| KOK 10071 | Polymer enhancer | 0.250% g % | 0–10.0 g % |
| Water insoluble inhibitor | See Table 4 | 0.025% and 0.1% | 0.01 to 4 g % |

What is claimed is:

1. In the semi-quantitative analysis of an aqueous test sample for human serum albumin which test sample is suspected of containing human serum albumin as well as other proteins and which analysis is carried out by contacting the fluid suspected of containing the proteins with a test reagent comprising a protein error indicator dye and buffer which dye undergoes a detectable color change when contacted with the proteins, the improvement which comprises adding to the test reagent a competitive inhibitor which is a polymer characterized by the formula:

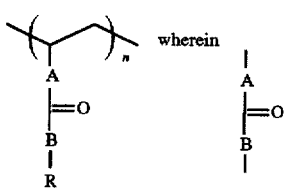

is a linking group in which A and B can either be a single bond or oxygen so that when A is oxygen and B is a bond the polymer is a poly(vinyl alkyl ester), when A is a bond and B is oxygen the polymer is a poly(alkyl acrylate), when A is oxygen and B is oxygen the polymer is a poly(vinyl alkyl carbonate) and when A is a bond and B is a bond the polymer is a poly(vinyl alkyl ketone) and R is a straight, branched or cyclic alkyl groups of 1 to 20 carbon atoms in which 0 to 10 hydrogens are replaced by hydroxyl groups and the polymer backbone comprises repeating alkyl or carbohydrate sub-units which can be copolymerized with unreactive blocking units and the number of alkyl groups attached to repeating polymer sub-units through the linking groups ranges from 10% to 90% of the theoretical maximum to thereby inhibit the protein error indicator response to the human serum albumin to a lesser degree than the response to the other proteins.

2. The method of claim 1 wherein the polymer backbone is made up of repeating alkyl units.

3. The method of claim 2 wherein the repeating alkyl units are ethylene, propylene or butylene.

4. The method of claim 1 wherein the polymer backbone is made up of repeating carbohydrate units.

5. The method of claim 4 wherein the repeating carbohydrate units are acrylamide, cellulose or glucosamine.

6. The method of claim 1 wherein the unreactive block units are vinyl alcohol, ethylene oxide, propylene glycol, ethylene ethyl ether, vinyl methyl ether, maleic anhydride, acrylic acid, adipate or carbonate.

7. The method of claim 1 wherein the protein error indicator is a phenolsulfonophthalein dye.

8. The method of claim 1 wherein the protein error indicator is Tetrabromophenol Blue, 5',5"-dinitro-3',3"-diiodo-3,4,5,6-tetrabromophenolsulfonephthalein, Coomassie Brilliant Blue, Fast Green FCF, Light Green SF, pyrogallol red or pyrogallol pyrocatechol violet.

9. The method of claim 1 wherein the competitive inhibitor is a poly(vinyl alkyl ester).

10. The method of claim 9 wherein the poly(vinyl alkyl ester) is poly(vinyl hexanoate), poly(vinyl neodecanoate) or poly(vinyl decanoate).

11. The method of claim 9 wherein the competitive inhibitor is a poly(alkyl acrylate).

12. The method of claim 11 wherein the poly(alkyl acrylate) is poly(hexyl acrylate) or poly(decyl acrylate).

13. The method of claim 1 wherein the competitive inhibitor is a poly(vinyl alkylcarbonate).

14. The method of claim 13 wherein the poly(vinyl alkyl carbonate) is poly(vinyl i-butylcarbonate).

15. The method of claim 1 wherein the competitive inhibitor is a poly(vinyl alkyl ketone).

16. The method of claim 15 wherein the poly(vinyl alkyl ketone) is poly(methyl vinyl ketone).

17. The method of claim 1 wherein the aqueous fluid is urine.

18. A test device for the semi-quantitative determination of human serum albumin in urine which device comprises an absorbent carrier having absorbed therein a protein error indicator dye, a buffering agent and a competitive inhibitor as described in claim 1.

* * * * *